United States Patent
Obukowho et al.

(10) Patent No.: US 9,420,863 B2
(45) Date of Patent: *Aug. 23, 2016

(54) NEUTRALIZING HAIR COMPOSITIONS AND METHODS

(75) Inventors: Patrick Obukowho, Fords, NJ (US); Gary Grey, New York, NY (US); Mark Szelast, Walnutport, PA (US)

(73) Assignee: SPARTAN BRANDS, INC., New York, NY (US)

( * ) Notice: Subject to any disclaimer, the term of this patent is extended or adjusted under 35 U.S.C. 154(b) by 526 days.

This patent is subject to a terminal disclaimer.

(21) Appl. No.: 12/851,369

(22) Filed: Aug. 5, 2010

(65) Prior Publication Data

US 2011/0253161 A1    Oct. 20, 2011

Related U.S. Application Data

(63) Continuation-in-part of application No. 12/760,108, filed on Apr. 14, 2010.

(51) Int. Cl.
| | | |
|---|---|---|
| *A45D 7/04* | (2006.01) | |
| *A61Q 5/04* | (2006.01) | |
| *A61K 8/36* | (2006.01) | |
| *A61Q 5/12* | (2006.01) | |

(52) U.S. Cl.
CPC . *A45D 7/04* (2013.01); *A61K 8/361* (2013.01); *A61Q 5/04* (2013.01); *A45D 2200/25* (2013.01); *A61Q 5/12* (2013.01)

(58) Field of Classification Search
CPC .......... A61K 8/922; A61K 8/06; A61K 8/31; A61K 8/361; A61K 8/416; A61K 8/43; A61K 8/8147; A61K 8/84; A61K 8/891; A61K 9/02; A61K 2800/21; A61K 2800/413; A61K 2800/88; A61K 2800/884; A61K 8/062
See application file for complete search history.

(56) References Cited

U.S. PATENT DOCUMENTS

| | | | | |
|---|---|---|---|---|
| 4,347,237 | A | * | 8/1982 | Evenstad et al. .............. 424/433 |
| 4,373,540 | A | * | 2/1983 | de la Guardia .............. 132/204 |
| 5,565,216 | A | * | 10/1996 | Cowsar et al. ................ 424/704 |
| 5,705,147 | A | * | 1/1998 | Shapiro ................. A61K 8/361 |
| | | | | 424/70.1 |
| 6,007,585 | A | * | 12/1999 | Syed et al. ........................ 8/432 |
| 6,562,328 | B2 | | 5/2003 | Pereira |
| 6,562,356 | B2 | * | 5/2003 | Verite et al. .................... 424/401 |
| 2004/0101501 | A1 | * | 5/2004 | Chen et al. ................. 424/70.12 |
| 2008/0085251 | A1 | * | 4/2008 | Shibuya .................... A61Q 5/04 |
| | | | | 424/70.5 |
| 2009/0074683 | A1 | * | 3/2009 | Nguyen et al. .................. 424/59 |
| 2009/0081147 | A1 | * | 3/2009 | Shibuya ................. A61K 8/447 |
| | | | | 424/70.5 |

OTHER PUBLICATIONS

Croda specialty ingredients for personal care, second edition. Copyright Nov. 2005, pp. 1-62.*
Biomimetic hair care ingredient from Croda, Cosmetics design.com. Published Jan. 13, 2005. Accessed online Jun. 29, 2012.*
Croda Personal Care, Cutissential 18-MEA 40, product details. Accessed online Jun. 29, 2012.*
"The HLB System a time-saving guide to emulsifier selection", ICI Americas, Inc. http://www.firp.ula.ve/archivos/historicos/76Book HLB ICI.pdf, accessed online Feb. 5, 2013.*

* cited by examiner

*Primary Examiner* — Audrea Buckley
(74) *Attorney, Agent, or Firm* — Tarter Krinsky & Drogin LLP

(57) ABSTRACT

The present invention is directed to methods, compositions and kits for neutralizing alkaline hair. The present invention is also directed to methods, compositions and kits for straightening human hair. The methods comprise neutralizing the hair with a hair neutralizing composition comprising at least one fatty acid. The compositions comprise neutralizing compositions comprising at least one fatty acid. The kits comprise an alkali hair relaxer or components for preparing such a relaxer and the hair neutralizing compositions.

14 Claims, No Drawings ial form, in
NEUTRALIZING HAIR COMPOSITIONS AND METHODS

CROSS-REFERENCE TO RELATED APPLICATIONS

This application is a continuation-in-part application of U.S. patent application Ser. No. 12/760,108 filed Apr. 14, 2010, which is hereby incorporated by reference in its entirety.

TECHNICAL FIELD

This invention relates generally to compositions, kits and methods for neutralizing hair that is alkaline, such as hair that has been treated with an alkali relaxer in a straightening process, wherein fatty acid, or compositions comprising fatty acid such as oils containing a fatty acid, are used to neutralize and normalize the pH of the hair.

BACKGROUND OF THE INVENTION

Hair relaxers are used for permanent straightening of curly and/or kinky hair. Such products may be used by women of various ancestries, such as African, North or South American, Asian, Middle Eastern or European ancestry, who may have curly or kinky hair that they may wish to straighten or relax. The relaxer is typically an alkali (that is, a base having a pH that is higher than neutral) that breaks the natural disulfide bonds within the hair. The user mechanically straightens the hair. Then the disulfide bonds are essentially "reformed" in the straightened hair in conjunction with neutralization of the active ingredient in the relaxer, which is often a strong alkali.

The alkali relaxers for which the neutralizing compositions and methods of the present invention are applicable include those comprising a strong alkali. The neutralizing compositions and methods contained within may also work on a weak alkali, such as monoethanolamine, triethanolamine, and ammonium hydroxide, which may be used to lessen the degree of curl by weakening the disulfide bonds. In addition to breaking the disulfide bonds, these types of relaxers also tend to have the undesirable effect of stripping the fatty acids from the hair, leading to weak, dry and brittle hair.

There are two common types of alkali hair relaxers. The first type is known as a "lye relaxer," and includes formulations that contain sodium hydroxide, lithium hydroxide, or potassium hydroxide (the alkali earth metal hydroxides). These lye relaxers are usually supplied in cream form and are applied directly to the hair. Lye relaxers were developed in the early part of the 20$^{th}$ century. Because of the inherent dangers to hair and skin of sodium hydroxide and other alkali metal hydroxides, lye relaxers are usually relegated to the professional sector of the hair care market.

The second type of alkali relaxer is known as a "no-lye relaxer." No-lye relaxers were developed in the 1970s and make up the bulk of the non-professional or home use market sector. A no-lye relaxer system comprises a precursor cream that contains an alkali earth metal hydroxide, such as calcium hydroxide, which is mixed with a liquid "activator" that contains a strong nitrogenous base, such as guanidine carbonate. The activator liquid and the precursor cream are mixed just prior to use. There is a chemical reaction between these components, such as between the calcium hydroxide in the precursor cream and the guanidine carbonate in the liquid. This reaction produces the hair relaxing agent in activated form, in this case, guanidine hydroxide, which becomes the active alkali in treating the hair.

Thus, a difference between a "lye relaxer" and a "no-lye relaxer" is that a lye relaxer does not require a separate activator to produce the active relaxing agent (e.g., the sodium hydroxide or lithium hydroxide). Another difference is in the chemical reaction products that result when the lye relaxers or no-lye relaxers are subsequently neutralized.

All alkali relaxers are meant to be applied to the hair for a specific period of time, after which they are to be rinsed off, and thereafter neutralized, to stop the action of the residual relaxer. Typically, the neutralizing is done by way of an acidic shampoo, and the hair is then conditioned with a rinse-out and/or leave-in conditioner. Generally, such acidic shampoos contain water soluble acids such as citric acid, ascorbic acid and the like, to further their goal of lowering the pH of the hair after relaxer treatment.

As a next step, the hair is often further shampooed or conditioned. Commercial products currently exist that may include oils and lipids as conditioning agents or as claim ingredients solely for marketing purposes. For example, a shampoo marketed for neutralizing purposes and known as "Elasta QP Soy Oil" available from Strength of Nature Co. (Savannah, Ga., USA) contains soy oil. In another example, a product known as "Soft & Beautiful®" is commercially available from Alberto-Culver Co. (UK) Ltd. Additionally, there is historical evidence to suggest that women have applied oils and products such as eggs to their hair for conditioning purposes.

However, the products historically and currently used are generally not adequate for neutralizing purposes for several reasons: first, where any fatty acids may be included in known hair care products, the amounts of fatty acids present are generally miniscule and generally not sufficient to neutralize the user's hair. Further, mixing fatty acid with alkaline relaxers in commercial formulations generally leads to neutralized relaxers, not neutralized hair. In fact, adding anything containing a fatty acid to a relaxer in accordance with known methods or compositions is not expected to provide neutralization to hair, as the material added is expected to saponify before it reaches the hair, and effectively becomes soap. For example, the combination of guanidine carbonate with fatty acids to produce guanidine soaps has also been the subject of studies in relation to their detersive effects, see Poliakoff et al., "Guanidine Soaps"; Industrial and Engineering Chemistry 335-337 (February 1948).

As yet another disadvantage of the known formulations, acidic shampoos generally contain water soluble acids (not fatty acids), and as such, present the expected problems of further stripping and damaging the hair. In fact, this is true of all shampoos, not just acidic neutralizing shampoos.

Relaxing human hair is a destructive and irritating process that is known to strip the hair of some or even all of its natural fatty acids, often leading to hair that is dry, brittle and dull. Neutralizing shampoos that are typically used after the relaxer can further strip away the fatty acids and other lipids due to their detergency effect. Thus, there is an ongoing need to develop compositions that relax human hair but avoid damage to the hair. The hair neutralizing compositions, systems, kits and methods of the present invention avoid at least some damage caused by the typical relaxing process.

SUMMARY OF THE INVENTION

The present invention is directed, in certain embodiments, to a method of neutralizing alkaline hair comprising applying a composition comprising at least one fatty acid to the hair, wherein the at least one fatty acid is present in an amount effective to neutralize the hair.

The present invention is directed, in other embodiments, to a method of straightening human hair comprising:
(a) applying an alkali relaxer to the hair; and
(b) applying a composition comprising at least one fatty acid to the hair,
wherein the at least one fatty acid is present in an amount effective to neutralize the hair.

The present invention is directed, in other embodiments, to a method of straightening human hair comprising:
(a) applying an alkali relaxer to the hair; and
(b) applying a composition comprising at least one fatty acid to the hair;
wherein step (b) alone is effective to neutralize the hair without further application steps beyond step (b).

The present invention is directed, in other embodiments, to a hair composition comprising:
(a) one or more fatty acids in an amount effective to neutralize alkaline hair; and
(b) a vehicle chosen from a solvent, a lipid, an ester or an inert carrier or any combination thereof.

The present invention is directed, in other embodiments, to a hair composition comprising: (a) a natural oil containing a fatty acid; and (b) at least one additional fatty acid in an amount effective to neutralize hair that has had an alkali relaxer applied to the hair.

The present invention is directed, in other embodiments, to a kit for straightening human hair comprising: (a) an alkali hair relaxer or components necessary for preparing an alkali hair relaxer; and (b) a hair neutralizing composition comprising at least one of a fatty acid or a natural oil containing a fatty acid.

The present invention is directed, in still other embodiments, to a method of neutralizing hair after relaxer has been applied to the hair, the method comprising the selection of a neutralizing composition comprising a vehicle and a fatty acid for application to hair, wherein the selection of the neutralizing composition is based on one or more of the following factors:
(a) the acid value of the fatty acid;
(b) the ability of the fatty acid to mimic the effects of fatty acids naturally present in hair;
(c) the concentration of the fatty acid in the vehicle used to apply the fatty acid to the hair;
(d) the quantity of the vehicle and therefore of the composition applied to the hair being neutralized;
(e) the quantity of relaxer remaining on the hair before it is to be neutralized, including the effect of rinsing of the relaxer from the hair;
(f) the strength or the pH of the remaining relaxer;
(g) the period of time during which the composition remains in the hair; and
(h) the hair type, texture and quality.

The compositions, kits and methods of the present invention provide a relaxation process that results in much less damage than methods currently known and used in the art; as well as superior results and hair with desirable properties, including softness, conditioned state, lack of brittleness and fewer broken strands of hair; as well as faster results.

DETAILED DESCRIPTION OF THE INVENTION

As described herein, when referring to the measurement of the pH of hair, the process used for measuring such a value involves taking hair tresses and soaking them in a predetermined amount of water for about 10 minutes, and thereafter measuring the pH of the water. As used herein, "alkaline hair" refers to hair that has a pH higher than neutral such that it would be desirable to lower its pH closer to neutral to avoid deleterious effects to the hair. For example, alkaline hair that is treated in accordance with certain embodiments of the present invention may have a pH above about 7, above about 8, above about 9, above about 10, about 11, above about 12 or above about 13.

As used herein, the terms "neutralize" and "neutralizing" refer to the step wherein the hair is brought closer to a neutral pH. As used herein, these terms are also used interchangeably with the terms "normalizing" or "normalize." In the current art of hair relaxing, neutralizing is the step that follows the application of the relaxer to the hair and subsequent rinsing of the relaxer from the hair. The neutralizing step is intended to halt the relaxing.

Compositions known in the art for relaxing hair tend to be alkaline and generally impart alkalinity to the hair; thus, neutralizing is typically done using an acidic neutralizing shampoo to bring the hair closer to a neutral pH. As used herein, "a neutral pH" refers to a pH in the range of about 6.5 to about 7.5. As used herein, the "neutralizing step" or "normalizing step" generally refers to the step wherein the hair that has been treated with the alkali relaxer (and is therefore generally at a pH significantly higher than neutral) is treated to lower its pH. Thus, for the purposes of the present invention, the "neutralizing" step involves merely lowering the pH or bringing it toward a neutral pH, not necessarily bringing it completely to a scientifically neutral pH (that is, a pH in the range of about 6.5 to about 7.5). Accordingly, as used herein, the phrase "effective to neutralize" means that neutralization has been successfully accomplished when the pH of the hair has been lowered so that it is closer to a neutral pH (not necessarily to a certain pH value).

In certain embodiments, the term "neutralizing" as used herein may encompass conditioning the hair. The present compositions are superior to those known in the art in part due to their ability both neutralize and condition hair in a single step or a single application (in certain embodiments, no more than a single step or a single application), such that a subsequent separate conditioning step is not needed; however, it should be noted for the purposes herein that when referring to the abilities of the present compositions to "neutralize" hair, such a step includes adequate conditioning of the hair such that no further application steps (such as, e.g., a second application of neutralizing composition, or the application of an additional conditioner) are necessary. This is true throughout the present disclosure, whether or not conditioning is separately mentioned.

The present invention is directed, in certain embodiments, to methods for straightening human hair, compositions useful in such methods, and kits embodying such methods and compositions. In certain embodiments, an alkali relaxer is applied to the hair. Then after the hair has been relaxed, the hair is neutralized by applying an amount of a neutralizing composition comprising at least one fatty acid that is effective to neutralize the hair. Fatty acids or natural oils containing a fatty acid may be used to neutralize or normalize the pH of human hair after a hair relaxer treatment.

In certain embodiments, the present invention is directed to a method of straightening human hair comprising:
(a) applying an alkali relaxer to the hair; and
(b) applying a composition comprising at least one fatty acid to the hair;
wherein step (b) alone is effective to neutralize the hair without further application steps beyond step (b). This provides a unique advantage to the methods and compositions of the present invention, in that the neutralizing can be accomplished in a single step and no more. That is, after the relaxing step, a stylist or consumer need apply the neutralizing compositions of the present invention in just one step, and this single-step application is sufficient to satisfy the consumer's desire for positive results quickly and with a minimum number of steps. In various embodiments, steps (a) and (b) are effective to bring the pH of the hair under about 8.2, under about 8, under about 7.8, under about 7.5, under about 7.3, under about 7, under about 6.8 or under about 6.5 without any additional treatment steps such as adding additional compositions to the hair. In other embodiments, additional neutralizing or conditioning steps may be applied to achieve a desired pH value as described herein, or step (b) may be repeated; for example, step (b) may be performed two, three or four times to achieve the desired pH values mentioned herein.

In various embodiments of the present invention, the neutralizing composition may be applied to the relaxed hair before or after the relaxer has been rinsed from the hair—that is, the present invention contemplates embodiments wherein the relaxer is first applied and then rinsed from the hair and then the neutralizing compositions applied, as well as embodiments wherein the relaxer is first applied and then left in the hair during the application of the neutralizing compositions, and then both are rinsed out together. The present invention further contemplates additional embodiments wherein the neutralizing composition is applied to the hair at any time in relation to the application of the relaxer to the hair—for example, in certain embodiments, the neutralizing composition may be applied to the hair at any one or more of the following times: before application of the relaxer, at the same time as, simultaneous or contemporaneous with, application of the relaxer (such as, for example, mixed with the relaxer and applied to the hair in a single step), or after application of the relaxer (such as, for example, after the relaxer has been rinsed off or after application of the relaxer but without rinsing off the relaxer). In certain embodiments, the methods of the present invention comprise (a) applying an alkali relaxer to the hair; and (b) applying a composition comprising at least one fatty acid to the hair, wherein at least one fatty acid is present in an amount effective to neutralize the hair; wherein step (a) is performed first, followed by rinsing off the alkali relaxer, followed by rinsing step (b). In other embodiments, the relaxer is left on the hair during step (b), and the method further comprises the steps of: (c) rinsing off the neutralized relaxer and any remaining residual relaxer from the hair.

Because some users may desire varying degrees of straightening, in certain embodiments it may be desirable or possible to adjust the degree of hair straightening achieved by the relaxer treatment by applying the neutralizing composition at various times before, during or after the relaxer application as outlined herein. This may be done, for example, as follows: (1) by mixing a neutralizing composition of the present invention into the relaxer and then applying the resultant mixture to the hair; or (2) by applying a neutralizing composition to the hair first, and then applying the relaxer to the hair (with or without first rinsing the neutralizing composition from the hair).

In certain embodiments, it may be desirable to leave the neutralizing composition in the hair, without rinsing it, as a "leave in" neutralizer.

In certain embodiments, the neutralizing compositions of the present invention may be useful not just for application to just-relaxed hair as way to neutralize the hair, but also to the scalp and hairline of a user as a neutralizing "base composition"—that is, as a composition that is applied to the user's skin, as a way to protect it from the relaxing compositions (not necessarily an alkaline composition). Many relaxer applications, including home relaxer kits and varieties of salon relaxers, require or recommend the use of such a base composition on the scalp and hairline prior to the use of the relaxer. The base composition provides a barrier to misapplied relaxer to prevent the relaxer from coming in to contact with the skin, since relaxer should be applied to hair, and only to hair that has not been previously relaxed. Relaxers are highly alkaline and can irritate the skin quite easily. Most base compositions currently used in the art are simply petrolatum with added color and fragrance. Gel base compositions have also been developed which are made of gelled mineral oil. The base compositions provide a physical barrier by way of their viscosity to prevent the relaxer from coming in to contact with the skin. In the embodiments contemplated herein, a "neutralizing base composition" can be made by the addition of fatty acid to a thick and substantive carrier. Neutralizing base compositions can also be made by using, as base compositions, thickened or naturally thick vegetable or animal oils or waxes containing fatty acids. Neutralizing base compositions can also be made by adding or suspending water soluble acids (not necessarily fatty acids) in any thick and substantive carrier. When relaxer comes in contact with a neutralizing base composition, the relaxer's irritation potential is reduced or eliminated thereby preventing irritation to the skin should the relaxer physically penetrate the base composition. Upon rinsing of the base composition and relaxer from the hair, after the relaxer manufacturer specified amount of time has passed, immediate neutralization of the hair and residual relaxer may take place upon the combination of the relaxer and base composition as it is rinsed from the hair and as the neutralizing base composition passes over the hair.

In another embodiment, the compositions of the present invention may be useful as a strand protector. Strand protectors are used in some hair relaxer processes to protect previously relaxed hair from coming in to contact with relaxer, since previously relaxed hair can be severely damaged by the subsequent application of relaxer. Various chemical formulations have been developed herein that form a physical barrier preventing misapplied relaxer from coming in to contact with previously relaxed hair. These "strand protectors" are applied to previously relaxed portions of the hair prior to relaxer application. In certain embodiments, the present invention is directed to a "neutralizing strand protector"—which works similarly to the "neutralizing base composition," with a difference that a high degree of viscosity is not as essential because the strand protector must flow around the hair to completely cover the relaxed hair, but not accumulate to the degree that it becomes hard to manage during the relaxer application.

In other embodiments, the present invention is directed to a method of neutralizing alkaline hair comprising applying a composition comprising at least one fatty acid to the hair, wherein the at least one fatty acid is present in an amount effective to neutralize the hair. In various embodiments, the at least one fatty acid in the composition is present in an amount effective to bring the pH of the hair under about 8, under about 7.8, under about 7.5, under about 7.3, under about 7, under about 6.8 or under about 6.5 after a single application of the composition, after no more than two applications of the composition, after no more than three applications of the composition or after no more than four applications of the composition.

Alkali Relaxer

As has been noted above, the relaxers with which the neutralizing compositions and methods of the present invention can be used include those comprising an alkali (that is, a basic or alkaline composition), such as, for example, a strong alkali. In addition to breaking the disulfide bonds, these types of relaxers can also strip the fatty acids from the hair. The embodiments of the present invention also contemplate weak alkali relaxers such as, e.g., monoethanolamine, triethanolamine or ammonium hydroxide and the like. For example, the embodiments of the present invention may be adapted for use either by a stylist or for home use, and for this reason, either strong alkalis or weak alkalis are contemplated. For the purposes of the methods and kits of the present invention, any alkali relaxer known in the art can be used to relax the hair prior to application of the neutralizing compositions discussed herein.

Fatty Acids and Natural Oils Containing a Fatty Acid

According to an article published in the journal LIPIDS, (Integral Lipids of Human Hair, Wertz and Downing; 1988 Vol. 23, No. 9, pp. 878-881) fatty acids make up the majority of the lipids found in human hair. Among the most prevalent are C16:0 (palmitic), C18:0 (stearic), C18:1 (oleic) and alpha-linoleic. By far the most prevalent fatty acid found in human hair is C21:0 anteiso, which is otherwise known as 18-methyl eicosanoic acid, abbreviated as "18-MEA." These and other fatty acids, individually or in combination, may be used as part or all of the hair neutralizing compositions in the practice of the present invention.

In certain embodiments of the present invention, the higher the fatty acid content in the compositions, the better. Generally, higher concentrations of shorter chained fatty acids are more desirable because the resultant composition will have a higher acid value (the acid value being a factor that could be readily determined by one of ordinary skill in the art). Of course, this is true only up to a point, as too high amounts of fatty acid may lead to over-acidified hair.

As used herein, the terms "oil" and "lipid" refer to the same thing, and are used interchangeably. In certain embodiments, the fatty acids may be present in a natural oil that contains one or more fatty acids. Such compositions are advantageous because they may enable restoration of the hair to a state closely approximating its condition prior to relaxation treatment. This state may also be referred to as the hair's "natural state." As used herein, the term "natural state" need not be limited to the actual natural state of the consumer's hair, but may include the natural state of hair that is desirable by the consumer and may not otherwise be achievable without application of chemicals or assistance of a stylist. It is possible, by choosing an appropriate natural oil, or a combination of oils whether natural, synthetic or both, and supplementing the oil or oils with one or more appropriate fatty acids, to provide an amount of fatty acid that will restore the hair to a state closely resembling its natural state.

As used herein, "natural oil" means any oil or lipid that is found to occur in nature or that is derived from an animal or plant. As used herein, "synthetic oil" means any oil or lipid that is not derived from an animal or plant. Examples of synthetic oils include mineral oil, paraffins, isoparaffins or petroleum oils. Examples of natural oils include those that will be discussed further below.

If the neutralizing composition includes a natural oil that contains a fatty acid, the natural oil also may also function as a solvent or carrier for applying the other components of the neutralizing composition to the hair. In certain embodiments, the natural oil is one that contains a fatty acid. In various embodiments, the fatty acids may be unsaturated, saturated or any combination thereof.

There are many natural oils containing a fatty acid that may be suitable for the methods and compositions of the present invention, including, but not limited to: canola oil, coconut oil, corn oil, cottonseed oil, flaxseed oil, olive oil, palm oil, safflower oil, soybean oil, and sunflower oil. Sunflower oil in particular is a good match in terms of cost, availability, and stability. It has a lower oleic acid content than some of the other oils listed; however, it has been found to be fairly cost-effective to supplement oleic acid to the sunflower oil in exemplary embodiments of the methods, compositions and kits of the present invention. It has been found that the oleic acid is particularly desirable for the formulations of the present invention, as it functions to bolster the neutralizing effect of the natural oil and to provide a further source of one of the most abundant fatty acids typically found in human hair. The use of one or more natural oils also provides a good carrier for applying the fatty acids contained therein to the hair. Thus, in a preferred embodiment of the present invention, the neutralizing compositions comprise sunflower oil and added oleic acid.

The quantity of fatty acids to be applied to neutralize the hair is herein described, in various embodiments, as an amount that is "effective to neutralize the hair" or as "an effective amount of fatty acid." As mentioned previously herein, "neutralize" does not require that the hair's pH be brought to a scientifically neutral pH, such as a pH that is exactly 7, but rather that it merely bring the hair closer to neutral pH than it was immediately after relaxing; therefore, to be "effective" the compositions and methods of the present invention need only accomplish that step. However, in various embodiments, the compositions and methods of the present invention are effective to neutralize the hair by bringing it to the point where the deleterious effects of the alkali relaxer are negated (the "deleterious effects" including, but not limited to, hair brittleness, dryness, damage, breakage and weakness). In various embodiments, the compositions and methods of the present invention are effective to neutralize the hair by lowering its pH under about 8.2, under about 8, under about 7.8, under about 7.5, under about 7.3, under about 7, under about 6.8 or under about 6.5.

The factors that may be considered in selecting an effective amount of fatty acid or the specific neutralizing composition for application to the hair include one or more of: a) the acid value of the fatty acid; b) the ability of the fatty acid to mimic the effects of fatty acids naturally present in hair; c) the concentration of the fatty acid in the vehicle used to apply the fatty acid to the hair; d) the quantity of the vehicle and therefore of the composition applied to the hair being neutralized; e) the quantity of relaxer remaining on the hair before it is to be neutralized, including the effect of rinsing of the relaxer from the hair; f) the strength or the pH of the remaining relaxer; g) the period of time during which the neutralizing composition remains in the hair; and h) the hair type, texture and quality.

These and other factors not listed may be used to determine the components of a particular neutralizing composition.

In certain embodiments, the fatty acid in the neutralizing compositions of the present invention is a fatty acid normally or typically found in human hair. As used herein, "normally or typically found in human hair" means that the fatty acid can generally be detected in normal, healthy human hair. In other embodiments, the neutralizing composition comprises a mixture of fatty acids which has a fatty acid distribution that closely matches the distribution of fatty acids contained in human hair. However, this is by no means essential for a successful composition or method of the present invention.

In certain embodiments, the compositions of the present invention are able to neutralize the hair effectively without the addition of any other acids other than fatty acids—that is, without any acids such as those typically found in acidic shampoos, e.g., water soluble acids that are not fatty acids. One benefit of neutralizing hair using an effective amount of fatty acid instead of a shampoo is that the hair becomes neutralized without further stripping away fatty acids and other lipids (as is the case with neutralizing shampoos known in the art). Furthermore, the neutralizing fatty acid(s) in the compositions of the present invention can potentially replace lost fatty acids, leaving the hair softer, stronger and less damaged, and in certain embodiments of the present invention, eliminating the need for an additional separate conditioning step.

In certain embodiments, the neutralizing fatty acid or the neutralizing compositions containing the fatty acid should be rinsed from the hair after application to avoid a greasy after feel. In other embodiments, such a rinsing step is not necessary. In yet other embodiments, the neutralizing compositions contemplated herein further comprise one or more surfactants or cleansers and may effectively clean the hair in addition to neutralizing it, such that a separate shampoo application is unnecessary. Indeed, in certain embodiments, the methods of the present invention further comprise cleaning the hair, wherein the neutralizing and cleaning occur concurrently with the single step of applying the composition.

Hair that has been relaxed and neutralized with a neutralizing shampoo tends to be hydrophilic, which is an unhealthy state for hair. When a neutralizing composition according to the present invention is used in place of an acidic neutralizing shampoo, the hair is more hydrophobic, which is a more healthy state. As used herein, "healthy" when used to refer to hair means hair that is hydrophobic and exhibits less damage from the relaxing process than unhealthy hair (damage including dryness, breakage and weakness). A further benefit of applying an effective amount of a neutralizing composition according to the present invention in place of a neutralizing shampoo is that the neutralizing and conditioning may be all accomplished in one step, as fatty acids have the ability to condition the hair through several different ways, for example, but not limited to, the process of refatting. This can avoid the two steps typically used currently after the relaxing step: neutralizing and then conditioning with two different applications.

In certain embodiments of the present invention, the neutralizing compositions of the present invention are anhydrous—that is, they contain, in various embodiments, substantially no free water, or absolutely no free water.

Indeed, in certain embodiments of the present invention, the present methods comprise the steps of: (1) relaxing the hair; and (2) neutralizing and conditioning the hair in a single step and no more. In other embodiments, the present methods comprise the steps of: (1) relaxing the hair; (2) neutralizing, conditioning and cleansing the hair in a single step and no more—indeed, in such embodiments, it is possible to either reduce, or avoid entirely, the number of any other necessary cleansing steps (such as shampooing) after application of the compositions of the present invention.

There are multiple goals for the neutralizing compositions and methods of the present invention, including the following: One is to neutralize the residual alkali on the hair. Another is to replenish the fatty acids that were stripped during the relaxing process. Another is to restore the hair's natural hydrophobic state. Yet another is, in certain embodiments, to obviate the need for a using a separate shampoo after a relaxer treatment.

18-MEA is an unusual long chain fatty acid typically found in mammalian hair, and seldom found naturally outside of mammalian hair. It is found predominantly in a surface layer of the hair, or cuticle, along with palmitic and oleic acids. A quaternized derivative of 18-MEA may be added to the neutralizing composition to at least partially compensate for the fatty acids that have been stripped from the hair during the relaxing process as is mentioned above. It has also been found to be useful as a conditioning agent for the hair. This quaternized version comes in the form of C10-40 isoalkylamidopropylethyldimonium ethosulfate. A 40% active version of this quaternized version of 18-MEA (in the solvent dipropylene glycol) exists as "Cutissential™ 18-MEA 40," a proprietary item from Croda, Inc. (Edison, N.J., USA). Therefore, in various preferred embodiments of the present invention, the neutralizing compositions comprise C10-40 isoalkylamidopropylethyldimonium ethosulfate. In certain embodiments, the neutralizing compositions may comprise one or more of the following: a natural oil containing a fatty acid, an additional fatty acid, and C10-40 isoalkylamidopropylethyldimonium ethosulfate.

Many fatty acids have been found herein to be effective for the neutralization of alkali relaxed hair. In certain embodiments of the present invention, any naturally occurring fatty acids of vegetable or animal origin may be useful for the compositions and methods discussed herein. For example, in certain embodiments, any fatty acid with a carbon chain length of 4 to 22 atoms (denoted C4-C22) would be desirable. In certain embodiments, any one or more of saturated, monounsaturated, and polyunsaturated acids are useful. As another example, the quasi-fatty acid acetic acid (C2) is known to have certain properties that make it miscible in water. These properties may make acetic acid desirable in certain embodiments of the present invention.

Fatty acids that are contemplated within this invention include, but are not limited to, any of the following: acetic acid (C2), butyric acid (C4 saturated), caproic acid (C6 saturated), caprylic acid (C8 saturated), capric acid (C10 saturated), lauric acid (C12 saturated), myristic acid (C14 saturated), palmitic acid (C16 saturated), stearic acid (C18 saturated), oleic acid (C18 monounsaturated), linoleic acid (C18 polyunsaturated), linolenic acid (C18 polyunsaturated), arachidonic acid (C20 polyunsaturated), 18-methyl eicosanoic acid (C21 anteiso) and behenic acid (C22 polyunsaturated).

Although all of these fatty acids are capable of "neutralizing" relaxed hair through saponification, test results indicate that in some embodiments, shorter chain fatty acids (for example, those with 10 or fewer carbons) may be even more effective than the longer chain fatty acids. Generally speaking, higher acid values are desirable.

In some embodiments, any fatty acid is desirable if it has a melting point in the range such that it will be in a liquid state at room temperature, thus providing ease of interaction with the excess alkali in the consumer's hair. In other embodiments, any fatty acid that is solid or has a melting point higher than room temperature is also desirable; for example, any form that can be made applicable to a user's hair, or easily distributed on the hair. Desirable fatty acids should also, in preferred embodiments, not exhibit a strong odor or an odor that cannot readily be masked to make the product more desirable to consumers. For example, it has been found that caprylic acid tends to have a strong odor, but can be added as a secondary supplement to improve the performance of the finished product at a level where the odor can be successfully masked.

In various embodiments, the neutralizing compositions of the present invention comprise an amount of a fatty acid, or a natural oil containing a fatty acid, that is in the range of about 2 to about 100%, about 5 to about 90%, about 10 to about 85%, about 15 to about 80%, about 20 to about 75%, about 25 to about 70%, about 30 to about 65%, about 35 to about 60%, about 40 to about 55%, about 45 to about 50%, or about 90 to about 100% of the total neutralizing composition. In certain embodiments, it has been found that the application of a composition comprising 100% commercially available USP or NE grade oleic acid is useful to neutralize the hair.

In other embodiments, it has been found that a neutralizing composition in accordance with the present invention comprising in particular about 1 to about 10%, about 2 to about 8%, about 2.5 to about 7% or about 3%, about 4%, about 5% or about 6% shorter chain fatty acids (for example, those with 10 or fewer carbons), is useful to neutralize the hair.

Vehicle or Carrier

It has been found herein that fatty acids will have a neutralizing effect if they are alone applied to the hair, and if they are applied to the hair as part of natural oils that contain a fatty acid. But in certain embodiments, it can be separately or additionally desirable to apply effective amounts of these acids in a vehicle or carrier that aids in the application to the hair. As used herein, the terms "vehicle" and "carrier" are used interchangeably and refer to the same thing. Such a vehicle may be, for example, a solvent (such as water, alcohol, organic solvents such as glycerin or ethoxydiglycol, or inorganic solvents) an inert carrier such as a lipid or an ester or a synthetic oil such as mineral oil, or any combination thereof. Useful vehicles also include creams, emulsions, gels, suspensions, surfactants, pastes, sprays, foams, and any vehicles that are useful in hair care products, will not degrade easily during storage and transportation, can provide easy delivery of the active ingredients to the consumer and will not pose a serious hazard or risk to a consumer or stylist.

In certain embodiments, the vehicle may comprise a surfactant to aid in rinsing of the neutralizing composition and any residual relaxer from the hair. In certain embodiments, the surfactant may be an oil soluble surfactant. An oil soluble surfactant may be particularly useful in embodiments wherein the neutralizing compositions of the present invention are anhydrous. However, desirable surfactants for the compositions of the present invention are not necessarily limited in such a manner, and need not be oil soluble.

A non-limiting example of a useful surfactant is lauroyl sarcosine. The lauroyl sarcosine is an acid precursor to sodium lauroyl sarcosinate, a cleansing surfactant commonly found in shampoos and body washes. It is an oil-soluble, acidic surfactant that fits well and is chemically compatible with the other components of the formula, and aids in the rinse off of the product from the hair. Other surfactants known in the art may work as well in providing the aid in rinsing off the product from the hair, and may include nonionic surfactants; for example, high HLB (hydrophilic-lipophilic balance) surfactants such as, but not limited to, Polysorbate-60, Polysorbate-80, PEG-60 castor oil or Oleth-20. In various embodiments, the surfactant may be present in amounts of, for example, about 0.5 to about 10%, about 1 to about 5%, or about 1.5 to about 4.5% or about 2 to about 4% of the neutralizing compositions.

In certain embodiments, the compositions and methods of the present invention may include one or both of the following: a natural oil containing a fatty acid; and a vehicle separately carrying an additional fatty acid. That is, only one or the other may be present, or any combination of both may be present. Whether and which to include depend on factors such as the amount of fatty acid desired to be delivered to the customer and the compatibility of the various ingredients in such a composition.

Other Ingredients

The compositions, methods and kits of the present invention may also include, in certain embodiments, one or more additional optional ingredients such as a fragrance or an antioxidant, which may help to prevent long term rancidity of the natural oil. Suitable fragrances include, e.g., fragrances containing benzaldehyde and any fragrances known in the art. Suitable antioxidants include, e.g., tocopherol acetate, BHT (butylated hydroxytoluene) and BHA (butylated hydroxyanisole).

In various embodiments, the fragrances or antioxidants, if present, may be present in the compositions herein in amounts of about 0.01 to about 1% or about 0.05 to about 0.5% of the compositions.

An exemplary embodiment of a neutralizing composition of the present invention including for use in a kit and for practicing a method of the present invention is as follows:

EXAMPLE 1

| Ingredient | Range (% by weight) |
| --- | --- |
| sunflower oil | 0-100 |
| oleic acid | 0-100 |
| Cutissential ™ 18-MEA 40 | 0-20 |
| lauroyl sarcosine | 0-5 |

EXAMPLE 2

Another exemplary embodiment of a neutralizing composition of the invention is:

(a) sunflower oil, 68.0%

(b) oleic acid, 30%

(c) C10-40 isoalkylamidopropylethyldimonium ethosulfate (and) Dipropylene Glycol, (component (c) is the INCI (International Nomenclature of Cosmetic Ingredients) name of a Croda Incorporated conditioning ingredient named Cutissential™ 18-MEA 40), 1.0%

(d) lauroyl sarcosine 1.0%

(e) a fragrance (f) an antioxidant

Sunflower oil may be obtained from Arista Industries (Wilton, Conn., USA); oleic acid may be obtained as "Emersol 213™" from Emery Oleochemicals (Cincinnati, Ohio, USA); and lauroyl sarcosine may be obtained as "Crodasinic L" from Croda, Inc. (Edison N.J., USA). Cutissential™ 18-MEA 40 is a mixture of C10-40 alkylamidopropylethyldimonium ethosulfate (a quaternized derivative of 18-methyl eicosanoic acid) and dipropylene glycol available from Croda, Inc. (Edison, N.J., USA).

The following exemplary formulations illustrate certain embodiments of the present invention.

EXAMPLE 3

Another exemplary embodiment of a suitable composition of the present invention is as follows:

(a) sunflower oil, about 60 to about 75%

(b) oleic acid, about 25 to about 35%

(c) C10-40 isoalkylamidopropylethyldimonium ethosulfate (and) dipropylene glycol, (component (c) is the INCI (International Nomenclature of Cosmetic Ingredients) name of a Croda Incorporated conditioning ingredient named Cutissential™ 18-MEA 40), about 0.5 to about 5%

(d) lauroyl sarcosine, about 0.5 to about 2%

(e) a fragrance (f) an antioxidant

EXAMPLE 4

| | Ingredient | Percentage (by weight) |
|---|---|---|
| A. | canola oil | 73.5 |
| | flaxseed oil | 15.0 |
| | palmitic acid | 10.0 |
| | Cutissential ™ 18-MEA 40 | 1.0 |
| | lauroyl sarcosine | 0.5 |
| B. | almond oil | 78.5 |
| | flaxseed oil | 10.0 |
| | palmitic acid | 10.0 |
| | Cutissential ™ 18-MEA 40 | 1.0 |
| | lauroyl sarcosine | 0.5 |
| C. | corn oil | 73.5 |
| | oleic acid | 25.0 |
| | Cutissential ™ 18-MEA 40 | 1.0 |
| | lauroyl sarcosine | 0.5 |

EXAMPLE 5

| | Ingredient | Percentage (by weight) |
|---|---|---|
| A. | canola oil | about 65 to about 80 |
| | flaxseed oil | about 10 to about 20 |
| | palmitic acid | about 5 to about 15 |
| | Cutissential ™ 18-MEA 40 | about 0.5 to about 2 |
| B. | almond oil | about 70 to about 90 |
| | flaxseed oil | about 5 to about 15 |
| | palmitic acid | about 5 to about 15 |
| | Cutissential ™ 18-MEA 40 | about 0.5 to about 5 |
| | lauroyl sarcosine | about 0.2 to about 2 |
| C. | corn oil | about 70 to about 80 |
| | oleic acid | about 20 to about 30 |
| | Cutissential ™ 18-MEA 40 | about 0.5 to about 2 |
| | lauroyl sarcosine | about 0.5 |

For both Examples 4 and 5 above, in formulations A and B, the flaxseed oil serves as the source for linoleic and linolenic acids. The three formulations A, B and C illustrate that various combinations of natural oils and fatty acids can be used to achieve an effective amount of a desired fatty acid distribution.

Other embodiments herein may be more generally described as follows: In certain embodiments, the composition comprises an effective amount of at least one fatty acid for neutralizing hair that is alkaline—for example, but not limited to, hair that has been straightened with an alkali relaxer. In other embodiments, the composition comprises one or more natural oils that contain a fatty acid, providing an effective amount of fatty acid for neutralizing the alkaline hair.

In further embodiments, the compositions of the present invention comprise an effective amount of one or more fatty acids in combination with one or more natural oils chosen so that the amount of total fatty acid is an amount effective to neutralize any alkali relaxer in the hair, and so that the overall fatty acid distribution of the combined natural oils and fatty acids resembles that found in natural hair.

In still further embodiments, the compositions comprise a combination of an effective amount of one or more fatty acids with one or more natural oils, and a conditioning agent in the form of a quaternized derivative of 18-methyl eicosanoic acid, which is the primary fatty acid found in natural hair. This conditioning agent may include, in certain embodiments, C10-40 isoalkylamidopropylethyldimonium ethosulfate, obtained as a 40% active solution in the solvent Dipropylene Glycol, under the trade name "Cutissential™ 18-MEA 40" from Croda, Inc. (Edison, N.J., USA).

In still further embodiments, the compositions comprise the combination of an effective amount of fatty acid(s) and natural oil(s) along with the quaternized 18-MEA derivative conditioning agent and an oil-soluble surfactant to aid in rinsing; and a fragrance and antioxidant to preserve the stability of the composition.

In an exemplary embodiment of the method and the composition of the present invention, the neutralizing composition comprises:

(a) a natural oil containing a fatty acid;
(b) a fatty acid;
(c) (a) and (b) together providing an effective amount of fatty acid;
(d) a quaternized derivative of 18-methyl eicosanoic acid; and
(e) an oil soluble surfactant.

In another preferred embodiment of the method and the composition of the present invention, the neutralizing composition comprises:

(a) sunflower oil (Helianthus Anuus Seed Oil);
(b) oleic acid;
(c) (a) and (b) together providing an effective amount of fatty acid;
(d) C10-40 isoalkylamidopropylethyldimonium ethosulfate (and) dipropylene glycol; and
(e) an oil soluble surfactant.

In the compositions discussed above, a fragrance and an antioxidant may optionally be present. Further, the percentage amounts of the surfactant, fragrance and antioxidant components fall within typical ranges of such components found in commercially available hair care products, and the percentage amounts of the natural oil and fatty acid should provide effective amounts for the purpose thereof, i.e., sufficient fatty acid for relaxer neutralization, and sufficient oil to provide a vehicle for applying the other components to the treated hair. If the composition includes a natural oil containing a fatty acid as well as additional fatty acid, the total amount of fatty acid present should be sufficient for relaxer neutralization.

The time of treatment for straightening a subject's hair with an alkali relaxer is, in various embodiments, in a range of about 5 minutes to about 45 minutes, about 10 minutes to about 30 minutes, about 15 minutes or about 20 minutes. After the time for treatment has elapsed, the hair should be neutralized in order to avoid potential damage or adverse effects to the subject's hair. The relaxing agent may be removed by a thorough rinsing of the subject's hair with water. The rinse is typically followed by a neutralizing step, which may be accomplished by the application of an effective amount of a neutralizing composition, as described above.

Alternatively, after applying the relaxer for a selected period of time and prior to rinsing the relaxer, the consumer or stylist may apply the neutralizing composition to the hair and then rinse off the neutralized relaxer and any remaining residual relaxer along with any remaining neutralizing composition from the hair, leaving the hair soft, shiny, clean, neutralized and easy to style further as desired. This alternative procedure allows for neutralization of the alkali relaxer before the introduction of additional water. There is evidence that some of the damage resulting from alkali relaxers comes during the rinsing of the relaxer cream, when water can easily enter into hair that is in a swollen state. The ability to neutralize the relaxer in the absence of water, allowing the hair shaft to de-swell, could help to prevent irreversible hair damage.

As a further alternative, the hair may be treated with an effective amount of a neutralizing composition and then rinsed, optionally followed by a second application of an effective amount of neutralizing composition. In certain embodiments, this second application may be followed by one or more subsequent applications of further effective amounts of neutralizing composition.

The neutralizing compositions discussed herein should be compatible with all alkaline relaxers currently on the market. The consumer or stylist may apply the relaxer to the hair, let the relaxer sit for the appropriate amount of time, and then rinse the relaxer completely from the hair. The consumer or stylist then may immediately and thoroughly apply the neutralizing composition to all parts of the hair that had been contacted by the relaxer. After letting the composition sit for a period of time (for example, about 10 to about 20 seconds, or about 5 to about 30 seconds, or up to about one minute, or up to about 90 seconds, or up to about two minutes), the composition may then be rinsed from the hair. While care must be taken to saturate all relaxed hair, there is no problem with the compositions of the present invention's coming into contact with the scalp or unrelaxed hair. The process of the invention is now finished. The hair can be further shampooed or conditioned if desired, but in certain embodiments these further steps are not necessary. Thus, the neutralizing compositions of the present invention may take the place of the neutralizing shampoo and/or neutralizing conditioner that is supplied with many relaxers or by salons.

The present invention also relates, in certain embodiments, to a kit for straightening human hair comprising: an alkali hair relaxer or components necessary for preparing such a relaxer, and a hair neutralizing composition comprising an effective amount of fatty acid. The hair neutralizing composition may be, in certain embodiments, in the form of a cream, emulsion, suspension, foam, liquid or paste or any other form that will not degrade easily during storage and transportation, and can provide easy delivery of the active ingredients to the consumer. The fatty acid is preferably a fatty acid normally or typically found in human hair. In other embodiments, the kit comprises an alkali hair relaxer or components required for preparing such a relaxer—including, for example, precursor cream that contains an alkali earth metal hydroxide, such as calcium hydroxide, along with a liquid "activator" that contains a strong nitrogenous base, such as guanidine carbonate. The kit may include instructions that the activator liquid and the precursor cream are mixed just prior to use, to promote the chemical reaction between these components, producing the hair relaxing agent in activated form, e.g., guanidine hydroxide. The kit may further comprise a hair neutralizing composition comprising fatty acid, e.g., a natural oil or any other vehicle containing fatty acid, to provide an effective amount of such fatty acid. The kit may even further comprise, for example, an instruction sheet, mixing stick, gloves, comb or other materials for convenience or ease of use by the consumer or stylist.

In other embodiments, the kit comprises an alkali hair relaxer or components for preparing such a relaxer and also comprises a hair neutralizing composition according to any of those described above.

EXAMPLE 6

A hair swatch neutralization test was conducted as follows:

Swatches of African kinky hair from International Hair Importers (Glendale, N.Y., USA), approximately 1.5-2.0 grams in weight, were relaxed with a sufficient amount of Spartan Brands Triple Gro regular strength relaxer. The relaxer had a pH of 13.37 and a lye content of 2.07%.

After a processing time of 20 minutes, the swatches were thoroughly rinsed with warm (about 105 degrees F.) tap water until all visible traces of relaxer cream were gone (about 30 to about 45 seconds). The swatches were then treated with various neutralizing compositions for about 45 seconds, whereupon they were rinsed once again with warm tap water until all visible traces of residue were gone (about 30 to about 45 seconds). The swatches were then placed in 50 mL of water and allowed to sit for 10 minutes, at which time the pH was measured. The pH of the water containing the swatches was measured and gave an indication as to the degree of neutralization of the hair swatches.

Two popular neutralizing shampoos were tested, as well as different neutralizing compositions in accordance with the present invention. To simulate practices commonly used in salons, sometimes multiple applications of the neutralizing compositions were used.

The following composition according to the present invention was the basis for the varieties tested: sunflower oil 67.3%; fatty acid supplement (including one or more fatty acids) 30.0%; conditioning agent 1.0%; Polysorbate-80 1.0%; fragrance 0.7%. Variations in this formula were contemplated; for example: sunflower oil about 40 to about 70%, fatty acid supplement (including one or more fatty acids) about 25 to about 50%, conditioning agent about 0.5 to about 2%, Polysorbate-80 about 0.5 to about 1.5%, fragrance about 0.2 to about 1%.

1. Hair swatch relaxed and rinsed but not neutralized: pH=10.26. This result served as a base result for comparison.

2. Design Essentials Neutralizing shampoo (a known neutralizing shampoo available from McBride Research Laboratories, Inc. of Decatur, Ga., USA): after 1 treatment pH=8.38; after 2 treatments pH=7.94.

3. Dark and Lovely Neutralizing shampoo (a known neutralizing shampoo available from Soft Sheen Carson LLC, New York, N.Y., USA): after 1 treatment pH=8.25; after 2 treatments pH=5.94.

In various embodiments, the "fatty acid supplement" (that is, the additional fatty acid that was added) was 30% of the formulation and included:

4. 30.0% Oleic acid: after 1 treatment pH=9.38; after 2 treatments pH=6.67.

5. 30% caprylic acid: after 1 treatment pH=6.21.

6. 20.0% oleic acid, 10.0% caprylic acid: after 1 treatment pH=6.81.

7. 27.0% oleic acid, 3.0% caprylic acid: after 1 treatment pH=8.43.

8. 23.5% oleic acid, 6.5% caprylic acid: after 1 treatment pH=6.71.

In various embodiments, the fatty acid supplement was 50% of the formulation and included:

9. 47.0% oleic acid, 3.0% caprylic acid: after 1 treatment pH=6.96

In certain embodiments, the following oils were tested alone—that is, the compositions comprised 100% commercially available USP or NE grades of oil and were each applied to a hair swatch after relaxing.

10. 100.0% sunflower oil: after 1 treatment pH=8.97

11. 100.0% oleic acid: after 1 treatment pH=6.76

12. 100.0% caprylic acid: after 1 treatment pH=4.34

13. 100.0% coconut oil: after 1 treatment pH=8.46

14. 100.0% mineral oil: after 1 treatment pH=10.15

The above results showed that neither of the neutralizing shampoos available on the market that were tested were able to produce effective neutralization with one application—that is, for each of the two known formulations that were tested, a minimum of two applications was needed. The natural oils, even with their high fatty acid contents, were not capable of producing adequate neutralization on their own; it was found that the formulations were more desirable when the natural oils were supplemented with additional fatty acids (as used herein, the term "fatty acid supplement" is used in the Examples to describe the addition of one or more fatty acids to the compositions of the present invention). The compositions of the present invention were found to be adequate to neutralize the hair in only a single step after the relaxation step.

Caprylic acid as a primary or secondary supplement appeared to produce a highly desirable degree of neutralization beginning at about 6.5% of the 30.0% supplemental fatty acid level. However, the malodor at this level was difficult to overcome. By increasing the total supplemental fatty acid level to about 50.0%, Caprylic acid at levels as low as 3.0% was found to produce effective neutralization. In certain embodiments, it was found that a composition comprising about 23.5% oleic acid along with about 6.5% caprylic acid provided a highly desirable degree of neutralization of hair with only a single step after the relaxing step. Synthetic oils, like mineral oil, which contain no fatty acids, produced no neutralization other than that attributable to simply rinsing with water. However, they could also be used as vehicles when mixed with fatty acid supplements to further increase the amount of fatty acid in the compositions.

Coconut oil, which contains a higher percentage of short chain fatty acids, was shown to produce a slightly higher degree of neutralization than sunflower oil. Palm oil would likely produce a similar result, based on its typical fatty acid distribution. These oils, however, have lower cloud points than other natural oils, which could provide cloudy compositions. Depending on the preference of users, this may or may not be a detraction from the visual desirability of the formulations and kits of the present invention.

There would appear to be many natural oils that may serve as the primary carrier for a neutralizing oil, as long as they are properly supplemented with additional fatty acids. Considerations such as stability, background odor, cost, availability, and commercial appeal must be taken when choosing appropriate natural oils. Suitable candidates may include, but are not limited to: corn oil, soybean oil, safflower oil, canola oil, olive oil, almond oil, wheat germ oil, and fish oils.

EXAMPLE 7

Further exemplary formulations in accordance with the present invention were prepared as follows:
A. sunflower oil—48.0%
oleic acid—about 46 to about 47%
caprylic acid—3.0%
conditioning agent—1.0%
high HLB surfactant—about 1 to about 2%
B. corn oil—85.0%
oleic acid—5.0%
caproic acid—10.0%
C. olive oil—87.0%
butyric acid—10.0%
surfactant—3.0%
D. mineral oil—30.0%
oleic acid—60.0%
caprylic acid—9.0%
emollient ester—1.0%

EXAMPLE 8

Further exemplary formulations in accordance with the present invention were prepared as follows:

A. sunflower oil—about 45 to about 50%
oleic acid—about 45 to about 50%
caprylic acid—about 1 to about 5%
conditioning agent—about 0.5 to about 2%
high HLB surfactant—about 0.5 to about 2%
B. corn oil—about 75 to about 90%
oleic acid—about 2 to about 10%
caproic acid—about 5 to about 15%
C. olive oil—about 80 to about 90%
butyric acid—about 5 to about 15%
surfactant—about 2 to about 5%
D. mineral oil—about 20 to about 40%
oleic acid—about 50 to about 70%
caprylic acid—about 2 to about 5%
emollient ester—about 0.5 to about 2%

EXAMPLE 9

Various compositions and methods in accordance with the present invention were tested using consumers and stylists. For Stylists 1 through 4 below, compositions were used having the following components: about 65 to about 70% sunflower oil; about 25 to about 35% oleic acid; about 0.5 to about 1.5% conditioning agent and about 0.4 to about 3% high HLB surfactant. In each case (unless otherwise indicated), the stylist applied the relaxer to the hair, then rinsed the relaxer from the hair, then applied and rinsed the neutralizing composition in accordance with the present invention. Results are summarized below:

Stylist Results #1

A first stylist stated that typically, she would apply the relaxer and then shampoo the client's hair at least twice (usually three times), followed by applying a deep conditioning treatment as well, which would be left on the hair for 5-10 minutes.

However, when using a composition and method of the present invention, she found that all she had to do was apply the relaxer, rinse the relaxer, then apply the composition, rinse it and then shampoo the hair only once. Thus, the stylist found that in total, she saved about 30 minutes by using the composition of the present invention, and only having to shampoo once (thus also saving on the amount of shampoo necessary after treatment with the neutralizing composition of the present invention).

Stylist Results #2

A second stylist stated that typically, she would apply the relaxer and then shampoo the client's hair three times, then apply a conditioner.

However, when using a composition and method of the present invention, after applying and then rinsing the relaxer, she applied the composition of the present invention and rinsed it. She then applied it a second time and rinsed it a second time. She found it unnecessary to shampoo or condition the client's hair. She found that she saved about 45 minutes. This even included time saved combing through the hair when wet, as she said it was much easier to do after application of a composition of the present invention.

Stylist Results #3

This was the first time that this stylist had used a composition of the present invention. She reported that it was easy to work with. The oil rinsed easily and it rinsed cleanly. The stylist did not shampoo the hair after the application. When the hair dried, it was soft and silky with a high sheen and no residue remaining on the hair. The stylist said that the hair felt really strong and said that it was much easier to work with in terms of combing through when wet.

The client said that after a relaxer her hair always feels dry and limp. She said that her hair had never been as soft as it felt after using the neutralizing composition of the present invention. She also loved the "natural" scent of the neutralizing composition and the shine it left on her hair. She believed that damaged hair would really benefit from the neutralizing composition.

Stylist Results #4

The stylist relaxed the hair, rinsed off the relaxer and then applied the composition of the present invention directly to the relaxed area of the hair; she applied slightly more with her hands to work the neutralizing composition through to the ends of the hair. She reported that the neutralizing composition rinsed cleanly—she did not have to shampoo the hair after rinsing.

Once dried, the hair had a high shine to it, which the client liked—she said that it made her hair look healthy. She also liked that the stylist did not need to use a sheen spray, which she felt makes her hair dirty quicker. She was impressed at how easily her hair was able to be combed through when wet without the use of a conditioning treatment.

The client also said that her hair felt like "it had been infused with nutrients"—it felt much softer and stronger than it usually would after a relaxer.

Stylist Results #5

For Stylist 5, the composition used had the following components: about 55 to about 65% castor oil; about 25 to about 35% oleic acid; about 5 to about 15% conditioning agent and about 0.4 to about 1% surfactant. A client returned 4 weeks after initial application of the composition of the present invention. The client was still happy and desired a second relaxer application with the neutralizing composition. She reported that her hair had felt extremely soft for about the first 2 weeks, but even after that softness faded, her hair still felt much stronger than usual and that she had noticed much less breakage after completion of the treatment.

EXAMPLE 10

Compositions in accordance with the present invention were subjected to testing as follows. The compositions comprised: about 65 to about 70% sunflower oil; about 25 to about 35% oleic acid; about 0.5 to about 1.5% conditioning agent and about 0.4 to about 1% surfactant.

I. Preparation of the Hair

Three formulations were tested and their results compared: Formulation "A" was commercially available "Motions Classic Neutralizing Shampoo," (available from Alberto-Culver USA, Melrose Park, Ill., USA). Formulation "B" was a commercially available "Olive Oil Creamy Aloe Shampoo" (available from Namaste Laboratories LLC, Blue Island, Ill., USA) and Formulation "C" was a neutralizing composition in accordance with the present invention.

"Kinky" hair (tresses that were approximately 1 inch wide, approximately 8 inches in length and approximately 3 g in mass) were obtained from De Meo Bros. (Jersey City, N.J., USA). For each of Formulations A, B and C, ten tresses were subjected to repeated brushing.

The protocol for applying Formulations A, B and C to the tresses was as follows:

1. While wearing plastic gloves, approximately 4 g of relaxer cream was applied to each tress. The relaxer cream was worked through with fingers until evenly distributed through the tress. Hair was smoothed with the flat end of a comb into a straightened position, which was then held for a total application time of 18 minutes.

2. Each tress was rinsed with warm water (35-40 C) until the relaxer cream was completely rinsed out.

3. For the first ten tresses, 1.5 g Formulation A was then applied to the tress for 30 seconds. Formulation A was then rinsed out with warm water (35-40 C) until completely rinsed out (about 30 seconds). Each tress was gently blotted to remove excess water, and then combed through twice with a medium-toothed comb. The tress was then allowed to dry at room temperature for an hour, with combing through once at 30 minutes and 60 minutes.

4. For the second ten tresses, the procedure in 3 above was performed with Formulation B.

5. For the third ten tresses, 2.0 g of a neutralizing composition according to the present invention was applied to the tress and worked through the tress with fingers until evenly distributed. As with the procedures for Formulations A and B, the neutralizing composition was then rinsed out with warm water (35-40 C) until completely rinsed out (about 30 seconds). Each tress was gently blotted to remove excess water, and then combed through twice with a medium-toothed comb. The tress was then allowed to dry at room temperature for an hour, with combing through once at 30 minutes and 60 minutes.

The tresses were then put into a constant temperature chamber and left overnight (at 21 degrees C. and 65% relative humidity).

II. Repeated Brushing Test

An automated device was used to provide repeated brushing of the tresses. Each tress was subjected to 100 brushes per minute, for a total of 1000 cycles of brushing (for each of tresses 1-10 for each of Formulations A, B and C). Results (number of broken fibers) are shown in Table 1 below, and statistical calculations are shown in Table 2 below.

TABLE 1

Comparison of Number of Broken Hair Fibers

| Treatment | 1 | 2 | 3 | 4 | 5 | 6 | 7 | 8 | 9 | 10 | Cumulative Total |
|---|---|---|---|---|---|---|---|---|---|---|---|
| Formulation A | 119 | 129 | 194 | 262 | 86 | 99 | 110 | 319 | 101 | 117 | 1,536 |
| Formulation B | 114 | 113 | 94 | 120 | 75 | 213 | 112 | 122 | 74 | 72 | 1,109 |
| Formulation C | 65 | 51 | 33 | 80 | 43 | 114 | 87 | 52 | 103 | 81 | 709 |

TABLE 2

Statistical Comparison of Number of Broken Hair Fibers

| Treatment | N | Mean | Standard Deviation | Std. Err. Mean |
|---|---|---|---|---|
| Formulation A | 9 | 135.2 | 56.68 | 18.89 |
| Formulation B | 10 | 110.9 | 40.95 | 12.95 |
| Formulation C | 10 | 70.9 | 26.53 | 8.39 |

As can be seen from the results, the hair treated with Formulation C showed a much lower cumulative total of broken fibers after repeated brushing, compared to the known Formulations A and B.

In sum, the results showed that a composition according to the present invention left the relaxed hair in a condition with a lower tendency to fiber breakage when compared to the two known treatments. Formulation C was 54% better than Formulation A and 36% better than Formulation B in reducing fiber breakage.

The compositions, methods and kits of the present invention have been found to be superior in neutralizing residual alkali in a user's hair, and restoring hair to a healthier state. Moreover, the compositions, methods and kits of the present invention have been found to be easy and time-efficient to apply, and obviate the need for additional conditioners and other hair products to provide a desirable end result with a minimum of expense.

Further, it is important to note that the compositions, methods and kits of the present invention are not restricted only to use with alkali hair relaxer treatments, but may be applied to other treatments of hair such as hair dyeing and bleaching, and other treatments that cause the hair to become alkaline after treatment. Thus, the present invention is directed, in certain embodiments, to a method of neutralizing alkaline hair comprising applying a composition comprising at least one fatty acid to the hair, wherein the at least one fatty acid is present in an amount effective to neutralize the hair. The alkaline hair may be alkaline due to being treated by, for example but not limited to, any of the following: (a) an alkali relaxer; (b) a hair coloring composition; or (3) a hair bleaching composition.

Most if not all permanent hair color contains either ammonia or MEA (monoethanolamine.) These can and do impart alkalinity to hair during the coloring process. Hair bleaches do the same using these and other chemicals. Rinsing with water is relied upon when coloring or bleaching the hair to bring the hair back to a neutral pH; however, rinsing with water may not be fully effective to neutralize hair. The effects of leaving the hair in an alkaline state are well known and include dryness, dullness and roughness, as already discussed herein. Further, it is known that alkalinity can change the color of the dyes used to color the hair. Hair dyes and bleaching compositions may also strip the hair of fatty acids. As discovered herein, fatty acids can be used to fully neutralize dyed or bleached hair. The benefits of neutralizing dyed or bleached hair with fatty acid include, for example, negating the previously mentioned detrimental effect of overly alkaline hair, imparting to the hair a conditioned effect, possibly replacing fatty acids that were stripped from the hair during coloring or bleaching, and stabilizing the color with effective neutralization.

Although the present invention has been described in relation to particular embodiments thereof, these embodiments and examples are merely exemplary and not intended to be limiting. Many other variations and modifications and other uses will become apparent to those skilled in the art. The present invention should, therefore, not be limited by the specific disclosure herein, and may be embodied in other forms not explicitly described here, without departing from the spirit thereof.

What is claimed is:

1. A method of stopping the relaxing of human hair that has been treated with an alkali relaxer during a relaxing procedure, the method comprising:
applying at least one fatty acid to the hair in a predetermined amount sufficient to stop the action of the relaxer, without the addition of any acid other than fatty acid.

2. The method of claim 1, wherein the fatty acid is present in the form of a natural oil.

3. The method of claim 1, further comprising cleaning or conditioning the hair.

4. The method of claim 1, wherein the conditioning is accomplished with a conditioning agent.

5. The method of claim 4, wherein the conditioning agent is a quaternized derivative of 18-methyl eicosanoic acid.

6. The method of claim 5, wherein the conditioning agent is C10-40 isoalkylamidopropylethyldimonium ethosulfate.

7. The method of claim 1, wherein the fatty acid is chosen from acetic acid, butyric acid, caproic acid, caprylic acid, capric acid, lauric acid, myristic acid, palmitic acid, stearic acid, oleic acid, linoleic acid, linolenic acid, arachidonic acid, 18-methyl eicosanoic acid and behenic acid.

8. The method of claim 1, further comprising contacting the hair with a high HLB surfactant.

9. The method of claim 1, further comprising applying at least one additional fatty acid to the hair.

10. The method of claim 9, wherein the at least one fatty acid is present in a vehicle chosen from a solvent, a lipid, an ester or an inert carrier or any combination thereof.

11. The method of claim 1, wherein the predetermined amount of the at least one fatty acid is effective to bring the pH of the hair under about 8 after a single application of the predetermined amount of fatty acid.

12. The method of claim 11, wherein the predetermined amount of the at least one fatty acid is effective to bring the pH of the hair under about 7.5 after a single application of the predetermined amount of fatty acid.

13. A method of straightening human hair, the method comprising the steps of:
(a) relaxing the hair by applying an alkali relaxer to the hair; and
(b) applying at least one fatty acid to the hair, in a predetermined amount sufficient to stop the relaxing, without the addition of any acid other than fatty acid.

14. The method of claim 1, wherein predetermined amount of the fatty acid is based on one or more of the following factors:
(a) the acid value of the fatty acid;
(b) the ability of the fatty acid to mimic the effects of fatty acids naturally present in hair;
(c) the concentration of the fatty acid in the vehicle used to apply the fatty acid to the hair;
(d) the quantity of the vehicle and therefore of the composition applied to the hair being neutralized;
(e) the quantity of relaxer remaining on the hair before it is to be neutralized, including the effect of rinsing of the relaxer from the hair;
(f) the strength or the pH of the remaining relaxer;
(g) the period of time during which the composition remains in the hair;
(h) the hair type, texture and quality; and
(i) the chain length of the fatty acid.

* * * * *